United States Patent
Greter et al.

(10) Patent No.: US 8,240,511 B2
(45) Date of Patent: Aug. 14, 2012

(54) DISPENSING ASSEMBLY WITH SEPARATE SYRINGES AND SYRINGE HOLDER

(75) Inventors: Andy Greter, Steinhausen (CH); Ralph Kayser, Lucerne (CH); Wilhelm A. Keller, Merlischachen (CH)

(73) Assignee: Medmix Systems AG, Rotkreuz (CH)

( * ) Notice: Subject to any disclaimer, the term of this patent is extended or adjusted under 35 U.S.C. 154(b) by 0 days.

(21) Appl. No.: 13/054,023

(22) PCT Filed: Jul. 3, 2009

(86) PCT No.: PCT/CH2009/000233
§ 371 (c)(1),
(2), (4) Date: Jan. 13, 2011

(87) PCT Pub. No.: WO2010/009563
PCT Pub. Date: Jan. 28, 2010

(65) Prior Publication Data
US 2011/0118664 A1    May 19, 2011

(30) Foreign Application Priority Data

Jul. 21, 2008 (CH) ...................................... 1134/08

(51) Int. Cl.
*B67D 7/70* (2010.01)
(52) U.S. Cl. ........................................................ 222/137
(58) Field of Classification Search ................... 222/137
See application file for complete search history.

(56) References Cited

U.S. PATENT DOCUMENTS

| | | | |
|---|---|---|---|
| 4,359,049 A | 11/1982 | Redl et al. | |
| 5,368,563 A * | 11/1994 | Lonneman et al. | 604/82 |
| 5,582,596 A * | 12/1996 | Fukunaga et al. | 604/191 |
| 6,840,921 B1 * | 1/2005 | Haider et al. | 604/191 |
| 7,468,049 B2 * | 12/2008 | Laveault | 604/82 |
| 2005/0027240 A1 | 2/2005 | Fehr et al. | |
| 2006/0116646 A1 | 6/2006 | Weiss | |
| 2007/0005020 A1 | 1/2007 | Laveault | |

FOREIGN PATENT DOCUMENTS

| | | |
|---|---|---|
| EP | 1 498 073 A1 | 1/2005 |
| WO | WO 2007/098624 A1 | 9/2007 |
| WO | WO 2008/001221 A2 | 1/2008 |

OTHER PUBLICATIONS

PCT International Search Report on application No. PCT/CH2009/000233 dated Nov. 6, 2009; 8 pages.

* cited by examiner

*Primary Examiner* — Christopher D Koharski
*Assistant Examiner* — Diva K Chander
(74) *Attorney, Agent, or Firm* — Foley & Lardner LLP

(57) ABSTRACT

The dispensing assembly has a one-piece syringe holder in which two separate syringes are placed and which includes a thumb rest that acts upon the thrust plates of the syringes jointly. The integral design of the syringe holder and the thumb rest results in a synchronous dispensing of both syringes. Preferentially, the syringe holder comprises guiding and fastening means for the separate syringes.

29 Claims, 3 Drawing Sheets

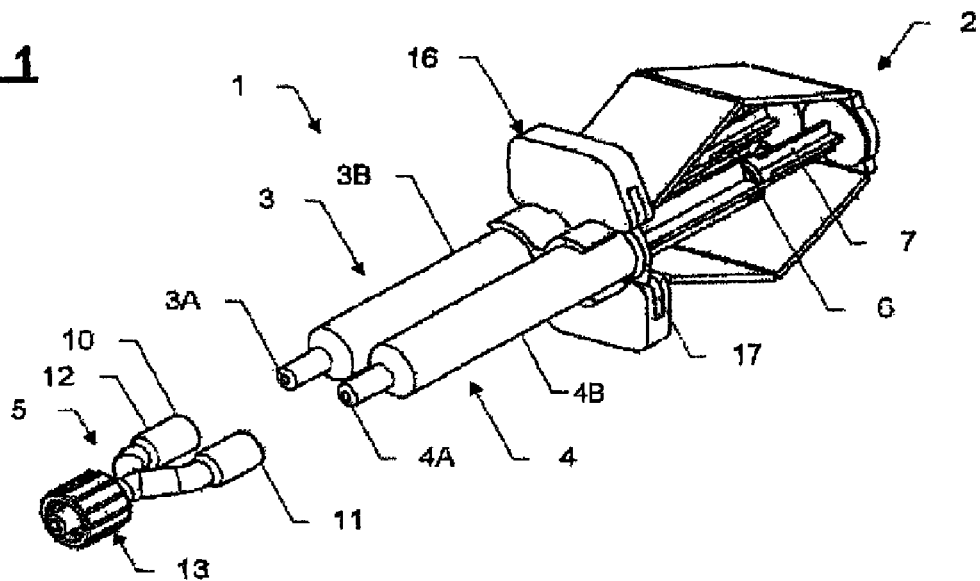
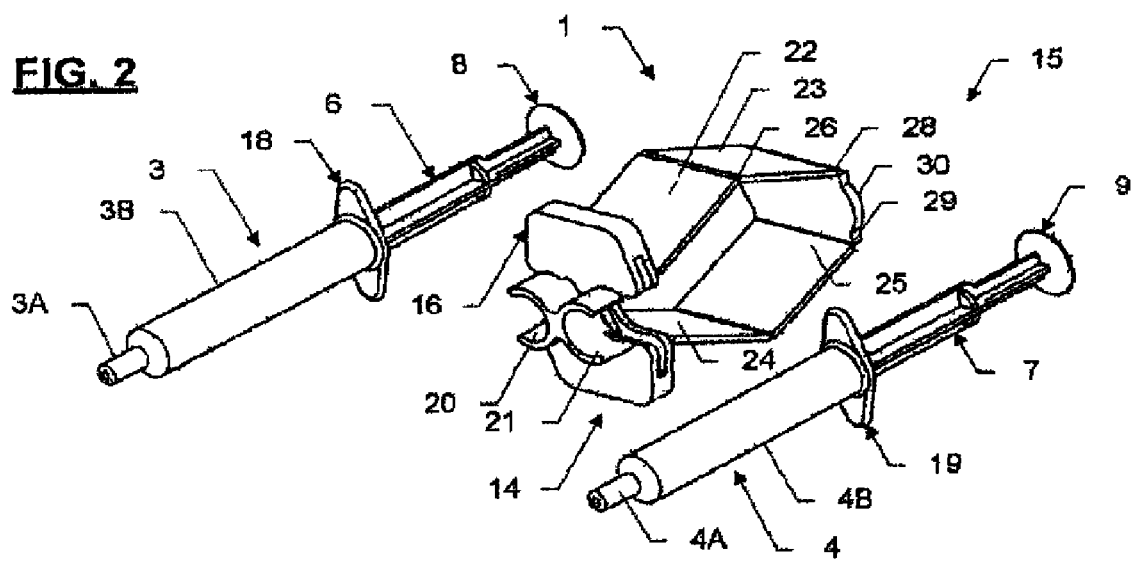
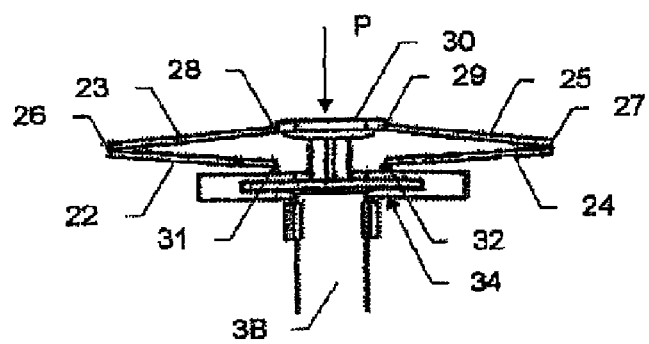

US 8,240,511 B2

DISPENSING ASSEMBLY WITH SEPARATE SYRINGES AND SYRINGE HOLDER

CROSS-REFERENCE TO RELATED PATENT APPLICATIONS

This application is a US National Phase of PCT application PCT/CH2009/000233 dated Jul. 3, 2009 and claims priority from Switzerland Application 01134/08, filed Jul. 21, 2008. All of the aforesaid applications are incorporated herein by reference in their entirety as if fully set forth herein.

FIELD OF THE INVENTION

The present invention relates to a dispensing assembly comprising at least two separate syringes and a syringe holder.

BACKGROUND OF THE INVENTION

Various designs of dispensing assemblies of this kind are known in the art, e.g. from WO-2007/098624 to the applicant of the present invention where a syringe holder is adapted to receive two separate storage containers and e.g. a mixer is attachable thereto, the pistons of the storage containers being moved forward by plungers. This device is appropriate for many applications but not for the use of conventional syringes that are to be dispensed jointly with a high mixing accuracy. US-2007/005020 discloses a double syringe comprising three distinct interconnected portions that allow jointly dispensing the syringes. In this simple construction, however, the guidance of the syringe plungers is not precise. This is also true for US-2006/116646 as well as WO-2008/001221.

SUMMARY OF THE INVENTION

On the background of this prior art, it is an object of the present invention to provide a dispensing assembly with separate syringes and a syringe holder that is simple in design and easy to operate, yet allows accurate metering due to a parallel and synchronous guidance of the plungers to achieve a precise mixing ratio.

This is accomplished by the dispensing assembly wherein the one-piece syringe holder is adapted to receive at least two separate syringes and has a thumb rest that acts upon the thrust plates of the syringes or the plunger ends.

BRIEF DESCRIPTION OF THE DRAWINGS

The invention will be explained in more detail hereinafter with reference to drawings of exemplary embodiments.

FIG. 1 shows a perspective view of a first exemplary embodiment of a dispensing assembly according to the invention, FIG. 2 shows separate parts of the assembly of FIG. 1, FIG. 3 shows the syringe holder of FIG. 2 in the actuated position.

DETAILED DESCRIPTION OF THE INVENTION

Figure 4:
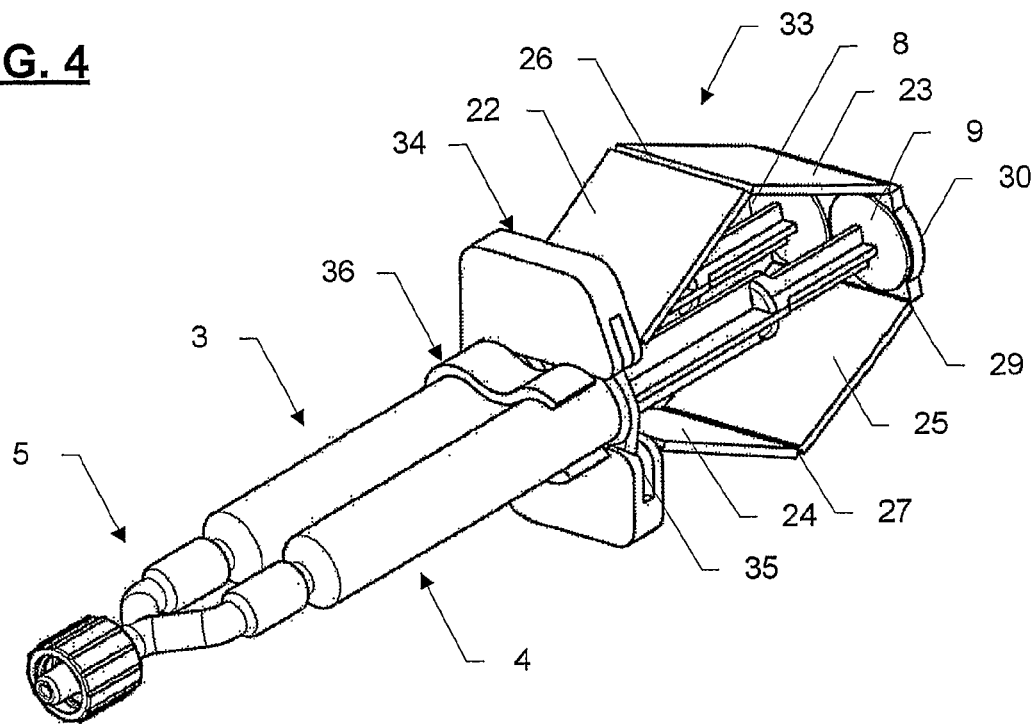
FIG. 4 shows a perspective view of an embodiment variant of the syringe holder in the assembly of FIG. 1.

FIG. 1 shows a first exemplary embodiment of an assembly 1 according to the invention including a syringe holder 2, two syringes 3 and 4, and an outlet adapter 5. In FIG. 2, the separate parts are illustrated, the syringes 3 and 4 in this exemplary embodiment having dispensing plungers 6 and 7 with thrust plates 8 and 9 and non-represented pistons. In the present case, the outlet adapter consists of two entrance portions 10 and 11 that are fitted onto the syringe outlets 3A and 4A and lead to a mixer 12 that may e.g. have a Luer-Lock outlet 13. Instead of a mixer, another outlet portion such as e.g. a spray head, a cannula or the like may be provided on the adapter.

Syringe holder 2 shown in FIG. 2 is made in one piece and preferably from synthetic material and essentially comprises two functional elements, namely a fastening portion 14 and an actuating portion 15. Fastening portion 14 has a flange 16 in each side of which a respective slot 17 for receiving the retaining flanges 18 and 19 of the syringes is arranged. On the outlet side, slots 17 are followed by respective snap guides 20 and 21 having an overequatorial circumference such that respective syringe containers 3B and 4B may be snapped in place therein. By slots 17 for the axial retention of the syringe containers, on one hand, and the snap guides for their lateral retention, on the other hand, a secure hold of the syringes is ensured.

On the other side of the retaining flange, actuating portion 15 is arranged which is preferably made from synthetic material and comprises five parts that are interconnected in a hinge-like manner. Seen from fastening flange 16, the actuating portion comprises two pairs of articulated parts 22 and 23 and 24 and 25, respectively, that are connected to each other by respective hinges 26 and 27. At one end, the articulated parts are connected via respective additional hinges 28 and 29 to a thumb rest 30 and at the other end by respective hinges 31 and 32 to fastening flange 16, the hinges in the present case being thinner portions between the articulated parts or between the articulated parts and the fastening portion. In the present example, the actuating portion is designed as a parallelogram.

In FIG. 3 it is schematically shown how actuating portion 15 is folded under the action of a pressure P. In this regard it is pointed out that the pressure applied by the thumb rest to the two thrust plates 8 and 9 is guided by the actuating portion in such a manner that a uniform, synchronous, and essentially linear discharge in the direction of the longitudinal axes of the syringes is ensured, thereby automatically guiding the plungers in parallel to one another.

Figure 5:
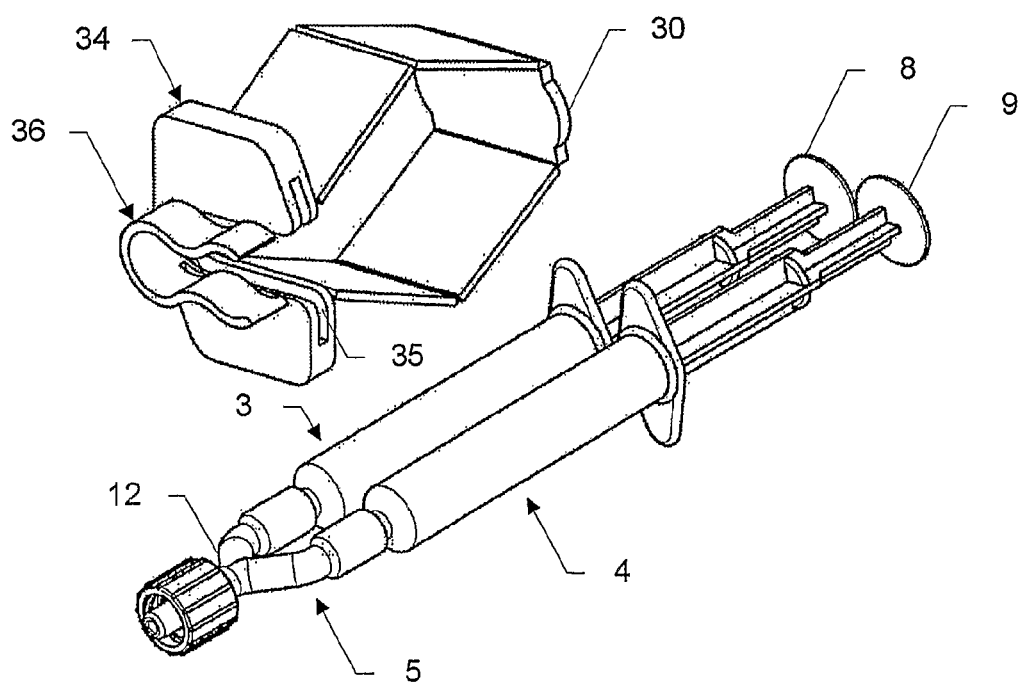
FIG. 5 shows separate parts of the assembly of FIG. 4.

In FIGS. 4 and 5, an embodiment variant of the syringe holder is illustrated where syringe holder 33 has the same articulated parts 22 to 25 and hinges 26 to 29 as well as 31 and 32 and thumb rest 30, but fastening flange 34 has a longer slot 35 in which both retaining flanges 18 and 19 of the syringes are received. Also, the two snap guides 36 are so designed that the two syringes, previously joined by means of the adapter, may be inserted one after another and fastened. In FIG. 5, the two parts, i.e. syringe holder 33 and the assembled syringes 3 and 4, are illustrated separately, and in FIG. 4, these two parts are inserted and ready for dispensing. The remaining parts including the mixer are the same as in the preceding exemplary embodiment.

Figure 6:
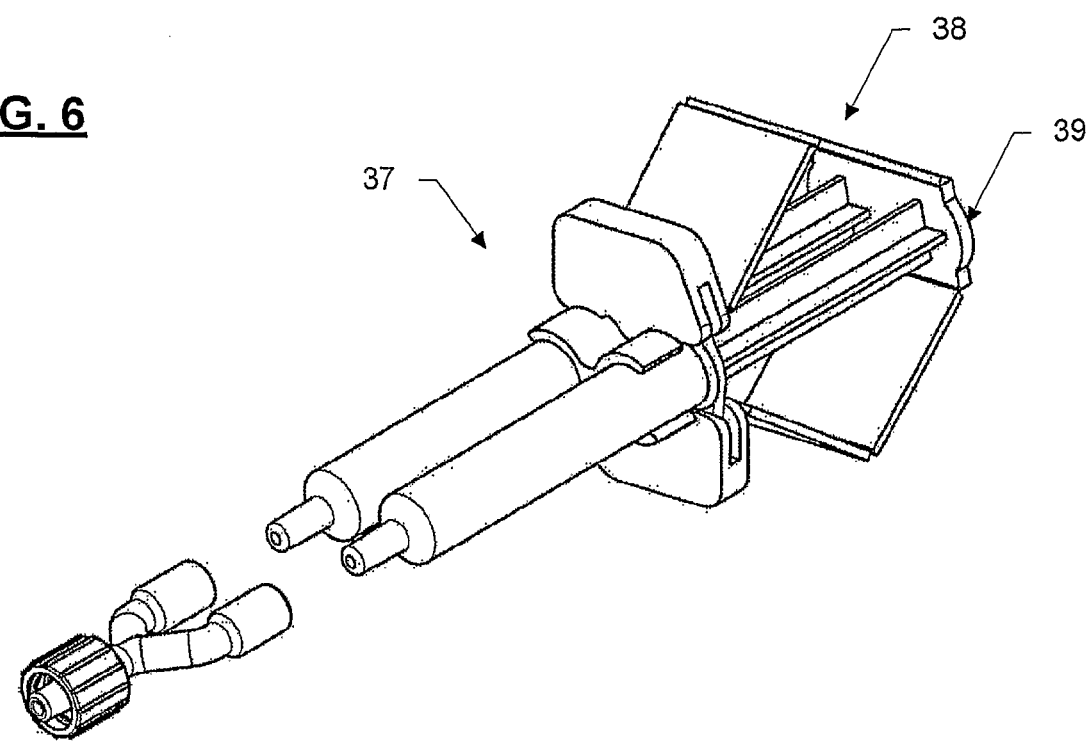
FIG. 6 shows a perspective view of a second exemplary embodiment of a dispensing assembly according to the invention.
Figure 7:
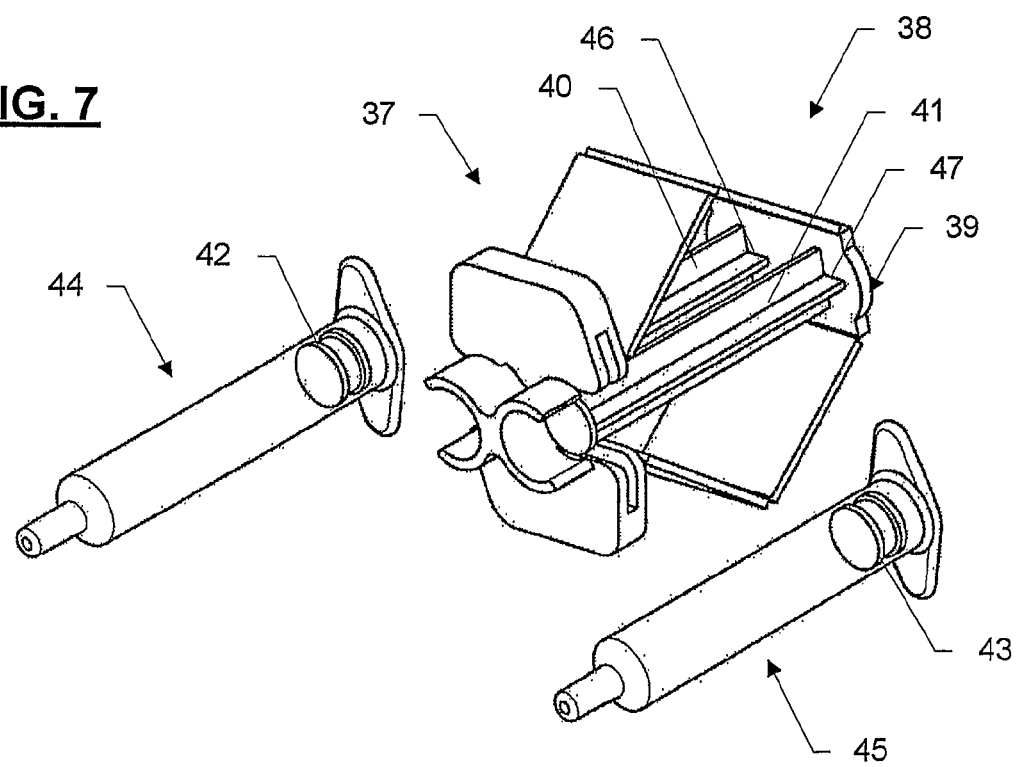
FIG. 7 shows separate parts of the assembly of FIG. 6.

In the second exemplary embodiment of a dispensing assembly 37 of the invention according to FIGS. 6 and 7, holder 38 is the same as that according to FIGS. 1 and 2 with the difference that on the inner side of thumb rest 39, two plungers 40 and 41 are arranged which act upon respective pistons 42 and 43 of syringes 44 and 45. In this manner, during dispensing, the pressure is again uniformly applied from thumb rest 39 to the ends 46, 47 of the plungers attached thereto. The remaining parts of the syringe holder, i.e. the fastening flange and the articulated parts, may be the same as according to FIGS. 1 or 2 or according to FIGS. 4 or 5. The operation of dispensing assembly 37 is also the same as in the first exemplary embodiment, the plungers being uniformly and safely guided in parallel to one another.

Based on the disclosed exemplary embodiments, it is possible to provide syringe holders and adapters that are designed for more than two syringes and allow simultaneously and uniformly dispensing all syringes. It is also possible to provide an actuating portion having more than two respective articulated parts which also essentially act as a parallelogram.

The invention claimed is:

1. A dispensing assembly comprising:
   at least two separate syringes, each of the at least two syringes including a syringe container and a plunger; and
   a syringe holder, configured to receive each of the at least two syringes, wherein the syringe holder includes:
      a fastening portion for retaining the syringe containers,
      a thumb rest that acts upon the plunger of each of the at least two syringes, and
      an actuating portion including articulated parts connected to the thumb rest, on one hand, and to the fastening portion, on the other hand, by hinges.

2. The dispensing assembly according to claim 1, wherein the articulated parts are interconnected by hinges to essentially form a parallelogram, for actuating the plungers in an essentially synchronous and parallel manner.

3. The dispensing assembly according to claim 2, wherein the actuating portion comprises two pairs of articulated parts.

4. The dispensing assembly according to claim 1, wherein each of the at least two syringes includes at least one retaining flange, and
   wherein the fastening portion includes at least one slot for receiving each of the at least one retaining flange of the at least two syringes.

5. The dispensing assembly according to claim 1, wherein the fastening portion includes snap guides for receiving the syringe containers.

6. The dispensing assembly according to claim 1, wherein the plungers connect to the inside of the thumb rest.

7. The dispensing assembly according to claim 1, wherein the outlets of each of the at least two syringes connects to an outlet adapter to which a dispensing member attaches.

8. The dispensing assembly according to claim 6, wherein the plungers and the thumb rest comprises one piece.

9. The dispensing assembly according to claim 1, wherein the syringe holder comprises one piece.

10. The dispensing assembly according to claim 1, wherein the syringe holder further includes a fastening flange defining an outlet side and a second side, the fastening portion on the outlet side of the fastening flange and the actuating portion on the second side of the fastening flange.

11. The dispensing assembly according to claim 1, wherein each of the plungers includes a thrust plate, and wherein the thumb rest acts upon each of the thrust plates.

12. The dispensing assembly according to claim 1, wherein each of the plungers includes a plunger end, the thumb rest acting upon the plunger ends.

13. A dispensing assembly comprising:
    at least two separate syringes, each of the at least two syringes including a plunger; and
    a syringe holder, configured to receive each of the at least two syringes, including:
       a thumb rest that acts upon the plungers,
       an actuating portion including articulated parts interconnected by hinges, the articulated parts essentially forming a parallelogram to actuate the plungers in an essentially synchronous and parallel manner.

14. The dispensing assembly according to claim 13, wherein the actuating portion comprises two pairs of articulated parts.

15. The dispensing assembly according to claim 13, wherein the syringe holder comprises one piece.

16. The dispensing assembly according to claim 13, wherein the syringe holder further includes a fastening flange defining an outlet side and a second side, a fastening portion on the outlet side of the fastening flange and the actuating portion on the second side of the fastening flange.

17. The dispensing assembly according to claim 16,
    wherein each of the at least two syringes includes at least one retaining flange, and
    wherein the fastening flange includes at least one slot for receiving each of the at least one retaining flange.

18. The dispensing assembly according to claim 13,
    wherein each of the plungers includes a thrust plate,
    wherein the thumb rest acts upon each of the thrust plates.

19. The dispensing assembly according to claim 13, wherein each of the plungers includes a plunger end, the thumb rest acting upon the plunger ends.

20. A syringe holder configured to receive at least two separate syringes, each of the at least two syringes including a syringe container and a piston in the syringe container, wherein a separate plunger acts on each of the pistons, the syringe holder comprising:
    a fastening portion for retaining the syringe containers;
    a thumb rest for actuating the plungers in an essentially synchronous and parallel manner; and
    an actuating portion including articulated parts connected to the thumb rest, on the one hand, and to the fastening portion, on the other hand, by hinges.

21. The syringe holder of claim 20, wherein the fastening portion, the actuating portion and the thumb rest comprise one piece.

22. The syringe holder according to claim 20, wherein the articulated parts are interconnected by hinges.

23. The syringe holder according to claim 20, wherein the articulated parts essentially form a parallelogram.

24. The syringe holder according to claim 20, wherein the actuating portion comprises two pairs of articulated parts.

25. The syringe holder according to claim 20, further comprising a fastening flange including an outlet side on which the fastening portion is arranged, and a second side on which the actuating portion is arranged.

26. The syringe holder according to claim 25, wherein the fastening flange includes at least one slot for receiving retaining flanges of the syringes.

27. The syringe holder according to claim 20, wherein the fastening portion includes snap guides for receiving the syringe containers.

28. The syringe holder according to claim 20, further comprising at least two plungers, wherein the at least two plungers connect to an inside of the thumb rest.

29. The syringe holder according to claim 20, wherein the plungers and thumb rest comprise one piece.

* * * * *